United States Patent [19]
Parker et al.

[11] Patent Number: 5,433,922
[45] Date of Patent: Jul. 18, 1995

[54] SELF-ADJUSTING TUBE DETECTOR

[75] Inventors: Nicholas Parker, Sunrise; Manuel Calvo, Miami; James N. Hoskinson, Sunrise; Kyriakos Christou, Miami Lakes, all of Fla.

[73] Assignee: Coulter Corporation, Miami, Fla.

[21] Appl. No.: 250,264

[22] Filed: May 27, 1994

[51] Int. Cl.⁶ .................. G01N 37/00; B67D 5/00
[52] U.S. Cl. ............................ 422/63; 422/65; 422/67; 422/100; 422/104; 436/47; 436/49; 436/54; 436/180
[58] Field of Search .............. 422/63, 65, 67, 104, 422/105, 107, 100; 436/43, 47, 48, 49, 50, 55, 54, 180; 73/864.91

[56] References Cited

U.S. PATENT DOCUMENTS

| | | | |
|---|---|---|---|
| 4,447,395 | 5/1984 | Englar et al. | 422/68 |
| 4,495,975 | 1/1985 | Harström et al. | 141/157 |
| 4,595,562 | 6/1986 | Liston et al. | 422/65 |
| 5,221,519 | 6/1993 | Wuerschum | 422/65 |
| 5,240,679 | 8/1993 | Stettler | 422/67 |
| 5,270,211 | 12/1993 | Kelln et al. | 436/43 |

*Primary Examiner*—James C. Housel
*Assistant Examiner*—Long V. Le
*Attorney, Agent, or Firm*—Mitchell E. Alter; John T. Winburn

[57] ABSTRACT

A self-adjusting tube detector for operating on a plurality of different types of collection containers or tubes including a pivotable adjustment arm which is biased into a first position. The first position is preadjusted for the smallest diameter tube to be utilized. When a larger tube is moved into the aspiration location, the adjustment arm is moved upward against the bias by the tube. The self-adjusting tube detector includes a pivotable reader arm, which is biased into a first position indicating the absence of a tube in the aspiration location. When a tube passes the adjustment arm, the tube will move the reader arm upward to provide a signal indicating that a tube is aligned in the aspiration location for aspiration by the stripper plate assembly.

7 Claims, 4 Drawing Sheets

SELF-ADJUSTING TUBE DETECTOR

BACKGROUND OF THE INVENTION

This invention relates generally to piercing specimen collection containers in an automated hematology analyzer. More particularly, the invention is directed to a self-adjusting tube detector for a hematology analyzer which can accept and verify a plurality of different sizes and types of collection containers.

Automated blood and blood cell analyzers are well known. These analyzers typically utilize a portion of a whole or pre-prepared blood sample. When the blood sample is taken from a subject, it usually is placed into a collection container such as a vial or test tube. With the potential of exposure to highly infectious diseases by an operator, such as the HIV virus or hepatitis, the tube is closed, typically by a rubber stopper. Many types of blood sample sampling devices have been developed, generally following the procedure of piercing the tube stopper to aspirate a portion of the blood sample. The needle probe or cannula then is removed from the tube and the stopper maintains the remainder of the blood sample sealed in the tube.

In automated hematology analyzers, such as a STKS hematology analyzer sold by the assignee of the present invention, Coulter Corporation of Miami, Fla., a plurality of the sample collection containers or tubes are placed into a tube carrier or cassette. The tube cassette then is loaded into the hematology analyzer and moved to an aspiration location. Each collection container or tube individually is moved to the aspiration location and pierced through its stopper by a transfer needle and a portion of the sample removed for analysis in the hematology analyzer.

Currently, there are four major types of tubes, each of which has a different size and shape. Alignment of each tube in the aspiration location is verified by a tube sensor or detector. Once the tube is verified to be at the aspiration location, the hematology analyzer includes a stripper plate which functions to align and seat the tube and stopper for piercing by the transfer needle. One universal stripper plate which preferably can be utilized in accordance with the present invention is disclosed in U.S. Ser. No. 08/250,265, entitled "Universal Stripper Plate", filed concurrently herewith and incorporated herein by reference.

Conventional tube sensors or detectors are adjusted to sense one size (diameter) of tube and generally have a narrow sensing range of tube diameters. For example, if the tube sensor or detector is adjusted and aligned for large diameter tubes, small diameter tubes can be missed altogether or misaligned in the aspiration location. Therefore, when it is desired to utilize another type of tube, the tube sensor or detector has to be adjusted and aligned to accommodate the other type of tube. This adjustment requires a service operation, since it is a critical adjustment to ensure that the tube sensor or detector is aligned and is operating correctly.

It therefore would be desirable to provide a self-adjusting tube detector which can accommodate a wide range of the various types and sizes of tubes, which allows full flexibility in handling the different tubes in the hematology analyzer.

SUMMARY OF THE INVENTION

The invention provides a self-adjusting tube detector for operating on a plurality of different types of tubes. The self-adjusting tube detector includes a pivotable adjustment arm which is biased into a first position. The first position is adjusted for the smallest tube to be utilized. When a larger diameter tube is moved into the aspiration location, the self-adjusting tube detector is moved upward against the bias by the tube. The self-adjusting tube detector includes a pivotable reader arm, which is biased into a first position indicating the absence of a tube in the aspiration location. When a tube passes the adjustment arm, the tube will move the reader arm upward to provide a signal indicating that the tube is aligned in the aspiration location for aspiration by the stripper plate assembly.

DESCRIPTION OF THE PREFERRED EMBODIMENTS

Figure 1:
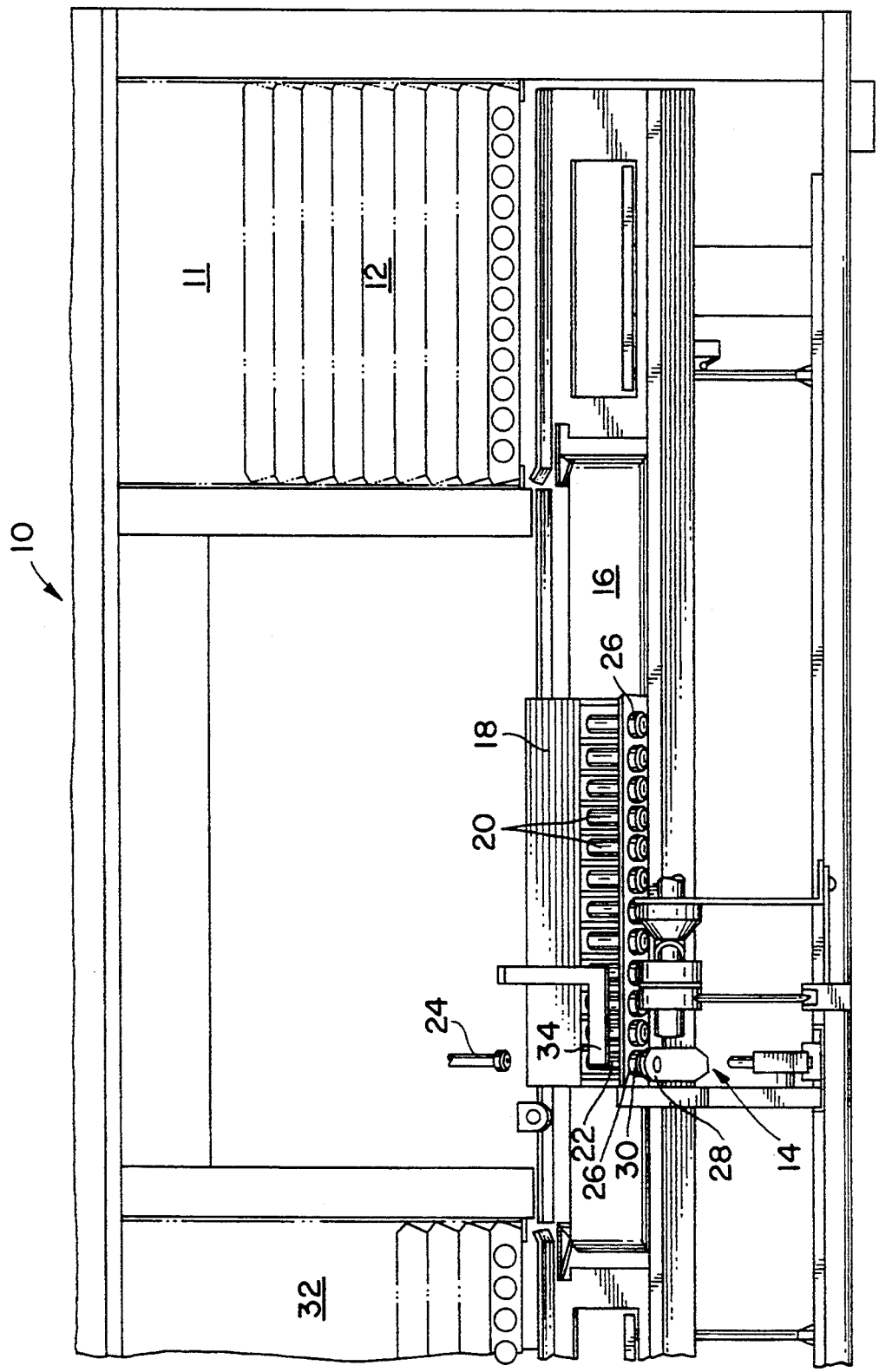
FIG. 1 is a front plan view of one hematology analyzer which can utilize the self-adjusting tube detector of the present invention.

Referring to FIG. 1, a hematology analyzer 10 is generally illustrated. Specific details of the operative components are more fully described in U.S. Pat. Nos. 3,549,994 and 4,609,017, which details are not considered essential for a description of the present invention. The hematology analyzer 10 includes a sample collection container or tube input area 11 including a plurality of tube carriers or cassettes 12, which are fed into a piercing and aspiration station 14 by a transport device such as a conveyor belt 16. One tube carrier or cassette 18 is illustrated in the aspiration station 14 containing a plurality of collection containers or tubes 20.

One tube 22 is aligned in an aspiration location and is aligned with a push rod 24, which will push the tube 22 partially out of the cassette 18. The push rod 24 pushes the tube 22 to abut a stopper or cap 26 of the tube 22 against a stripper bar or plate 28. The bar 28 includes a conventional stripper button 30, which aligns the cap 26 with an aspiration probe tip or needle (not illustrated), which is driven through the cap 26, typically by the push rod 24. After aspiration, the tube 22 is driven back into the cassette 18 in a conventional manner. One preferable aspiration operation is disclosed in cross-referenced application, U.S. Ser. No. 08/250,265, entitled "Universal Stripper Plate", which universal stripper plate would replace the conventional stripper bar or plate 28 and the conventional stripper button 30.

Each tube or collection container 20 is in turn moved into the aspiration location 14 and operated on in a similar manner. Once all the tubes 20 in the cassette 18 are aspirated, the cassette 18 is moved to an output area 32.

The correct position and alignment of the tube 22 in the aspiration location aligned with the axis of the aspiration needle (not illustrated) must be verified by a sensor 34. As previously referenced, the sensor 34 is located in a fixed position and cannot accommodate various size tubes.

Figure 2:
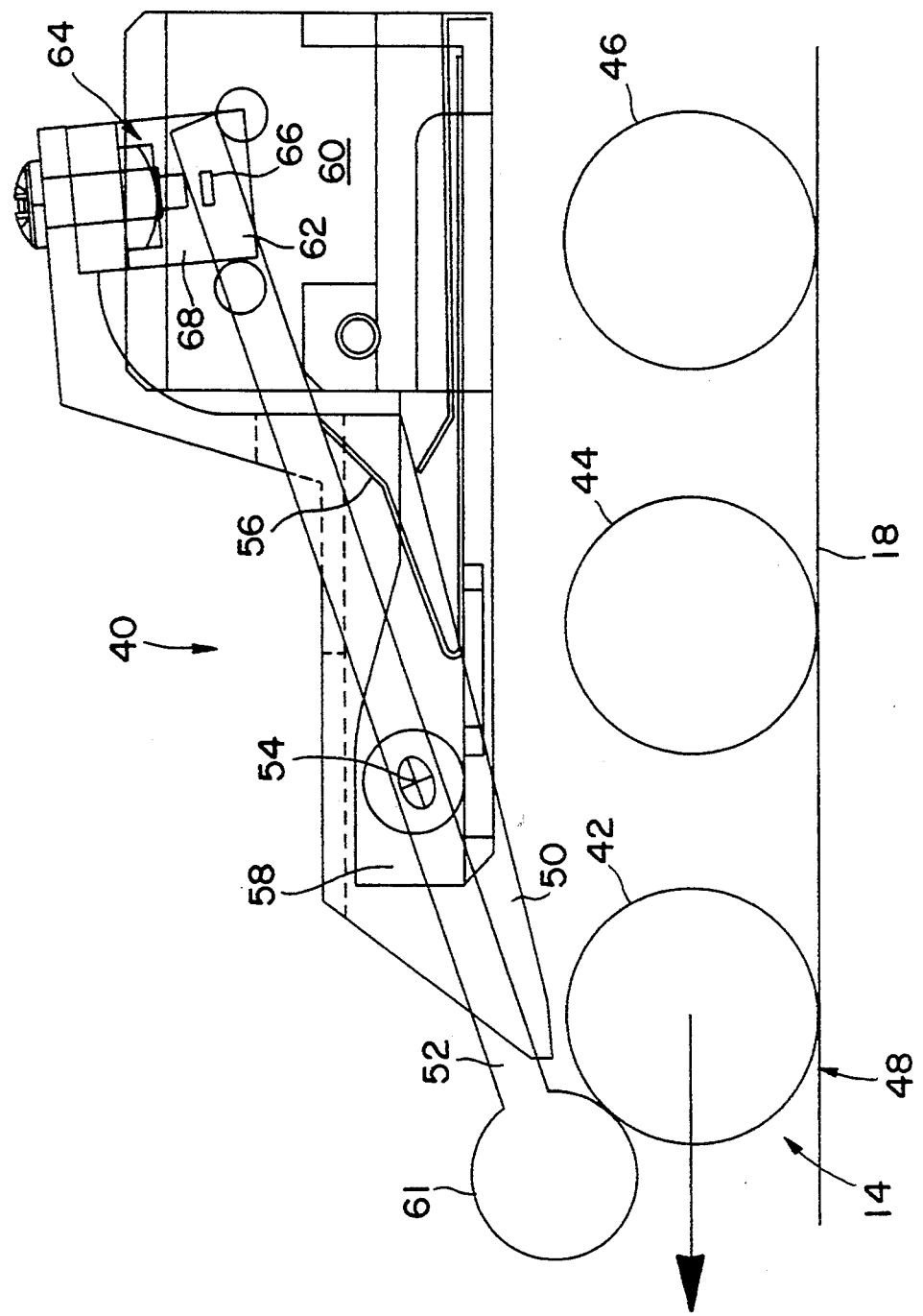
FIG. 2 is a side view of the self-adjusting tube detector of the present invention with small tubes.

Referring to FIG. 2, an embodiment of a self-adjusting tube detector of the present invention is designated generally by the reference numeral 40. The self-adjusting tube detector is similar in operation to the sensor 34 and would replace the sensor 34 in the hematology analyzer 10 as well as in similar tube sensing operations and analyzers.

The self-adjusting tube detector 40 is illustrated with a plurality of small diameter collection containers or tubes 42, 44 and 46. The tubes 42, 44 and 46 are illustrated moving to the left and generally would be moved in the cassette 18 (not illustrated in detail). The tube 42 is illustrated approaching an aspiration location 48, such as in the aspiration station 14.

The self-adjusting tube detector 40 is physically preset to accept larger tubes (FIGS. 3 and 4) and therefore the tube 42 passes under a pivotable adjustment arm 50, without contacting the adjustment arm 50. Only one adjustment arm 50 is illustrated and described, although a pair of adjustment arms 50 physically connected and functioning in unison are preferable. The adjustment arm 50 provides the flexibility for the self-adjusting tube detector 40 to act upon larger diameter tubes as will be described with respect to FIGS. 3 and 4.

Figure 3:
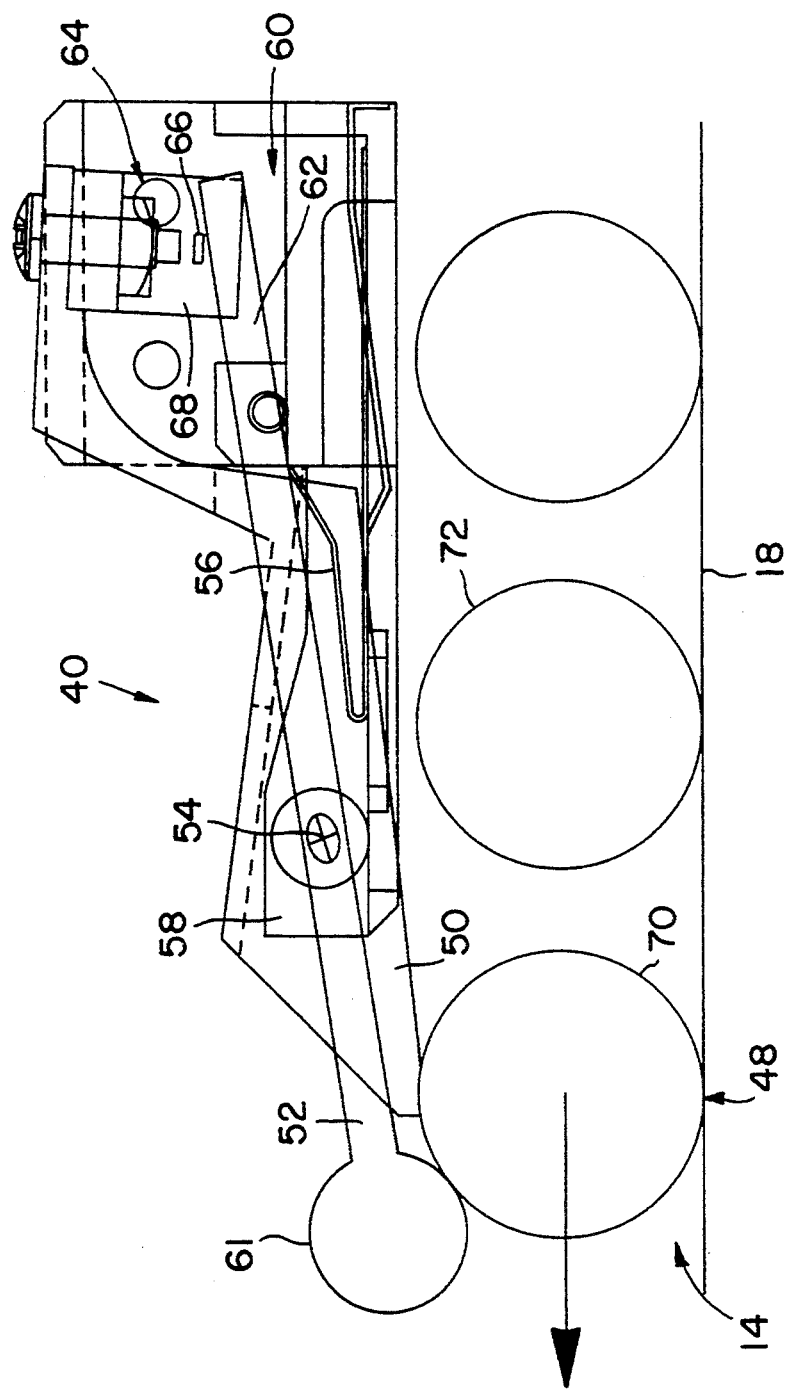
FIG. 3 is a side view of the self-adjusting tube detector of the present invention in an activated state.

The tube 42 starts to bear against a pivotable reader arm 52. The reader arm 52 is pivotably mounted on a pivot pin 54 and biased into a first position by a spring 56, as illustrated in FIG. 2. The pivot pin 54 and the spring 56 are mounted on a fixed frame portion 58 of a base body portion 60. The spring 56 or other biasing means maintains the reader arm 52 in the inactive position, but allows the tube 42 to move the reader arm 52 into an activated position (FIG. 3). The reader arm 52 preferably includes an enlarged rounded reader head or verification portion 61, which bears against the tubes as they move into the aspiration station 14 and the aspiration location 48.

The reader arm 52 also includes a light beam blocking end 62. The self-adjusting tube detector 40 includes a light beam source (not illustrated) in one side of a sensor 64 which generates a beam directed substantially perpendicular to the reader arm end 62. The light beam can be sensed by a sensor portion 66 in a second side 68 of the sensor 64. The sensor portion 66 is spaced from the light beam source sufficiently to allow the reader arm end 62 to move freely therebetween.

When a tube, such as a large diameter tube 70, illustrated in FIG. 3 is moved into the aspiration location 48, the adjustment arm 52 is pivoted upwardly around the pivot 54. This moves the reader arm end 62 against the spring 56 and when the tube 70 is in the aspiration location 48, as illustrated, the reader arm end 62 is moved out of the light beam path and the sensor 64 can receive the light beam at the sensor portion 66. The sensor 64 then sends a verification signal to the hematology analyzer 10, which then performs the aspiration operation on the tube 70. When aspiration of the tube 70 is completed, the cassette 18 is moved to the left to move the tube 72 into the aspiration location 48. As the tube 70 is moved past the reader arm head or verification portion 61, the spring 56 will bias the reader arm 52 back into the inactive position (FIG. 2), ready to verify the next tube 72.

Figure 4:
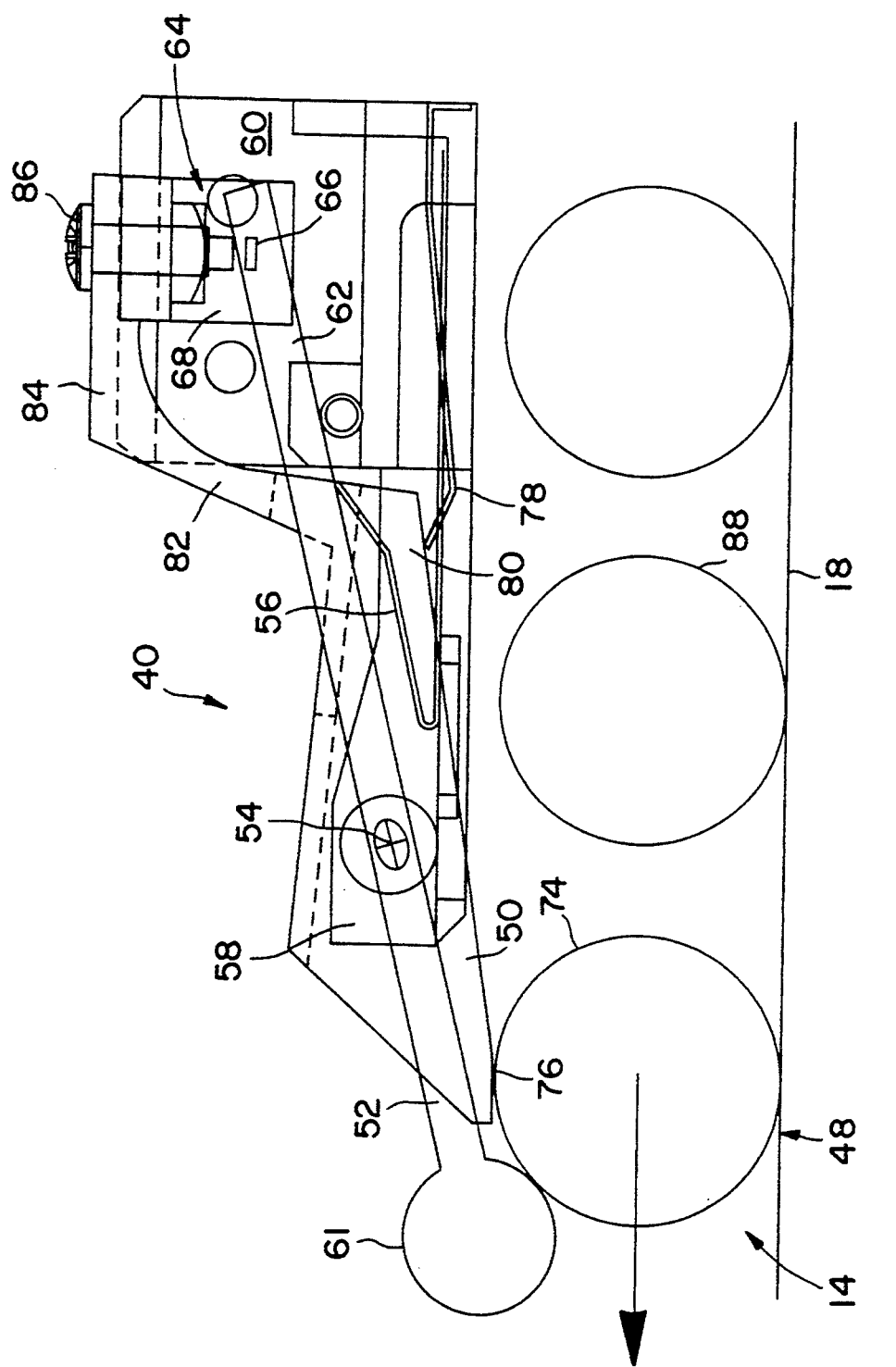
FIG. 4 is a side view of the self-adjusting tube detector of the present invention with large tubes.

FIG. 4 illustrates the main feature of the self-adjusting tube detector 40 of the present invention, operating again on a large diameter tube 74. As the tube 74 is moved into the aspiration station 14, the tube 74 first bears against a first end 76 of the adjustment arm 50. The adjustment arm 50 also is pivotably mounted on the fixed frame portion 58 of the self-adjusting tube detector 40, such as also on the pivot pin 54 and also is biased into a first position (FIG. 2) by a spring 78. The pivot pin 54 preferably is mounted between the pair of adjustment arms 50 (not illustrated), with the reader arm 52 mounted therebetween.

The spring 78 bears against an elbow or base 80 of an arm portion 82 of the adjustment arm 50. The arm portion 82 includes an end portion 84 upon which is mounted the sensor 64 by conventional means, such as a screw 86. The adjustment arm 50 thus pivots to adjust to the size of the larger tubes 70 or 74 and moves the whole verification assembly of the self-adjusting tube detector 40 to a location adjusted by the diameter of the tubes. This movement or adjustment from the first position (FIG. 2) ensures that a correct verification signal is generated when the tube is in the aspiration location 48. The spring 78 will bias the adjustment arm 50 back toward the first location as the tube 74 moves out of the aspiration location 48. Thus, the self-adjusting tube detector 40 will be in position for the next tube 88, without regard to the tube size.

Thus, the self-adjusting tube detector 40 accurately verifies the location of a tube in the aspiration location 48, without regard to the size of the tube within a size range. Further, one cassette can contain various tube sizes without requiring a physical adjustment of the location of the self-adjusting tube detector 40. The body portion 60 of the self-adjusting tube detector 40 can be mounted as desired in the aspiration station 14.

Although, the self-adjusting tube detector 40 can be utilized with a range of tube diameters, it preferably is utilized with the tube adapters disclosed in our U.S. Ser. No. 08/250,201, entitled "Tube Adapter", filed concurrently herewith and incorporated by reference. This combination further extends the range of tube diameter which can be utilized in the analyzer 10.

Many modifications and variations of the present invention are possible in light of the above teachings. The head or verification portion 61 preferably is rounded, but also can be of other shapes if desired. The springs 56 and 78 can be leaf springs as illustrated or can be other types of conventional biasing mechanisms. Other types of sensors 64 also could be utilized, such as magnetic, light reflective or contact type sensors. It is therefore to be understood that within the scope of the appended claims, the invention may be practiced otherwise than as specifically described.

We claim:

1. A self-adjusting tube detector, comprising:
   a pivotable reader arm having a first verification end biased for bearing against each one of a plurality of tubes in a predetermined size range, as each one of the tubes is moved into a verification location;
   at least a pivotable adjustment arm having a first end biased for bearing against tubes greater than a predetermined size within said size range being moved into said verification location;
   a sensor mounted on said adjustment arm;
   said reader arm including a second end which activates said sensor when a tube is moved into said verification location; and
   a detector body having said reader arm and said adjustment arm pivotably mounted on said detector body.

2. The detector as defined in claim 1 including a pair of adjustment arms spaced from one another, mounted on a pivot pin and operable together.

3. The detector as defined in claim 2 including said pivot pin extending between said pair of adjustment arms and said reader arm pivotably mounted on said pivot pin between said adjustment arms.

4. The detector as defined in claim 1, said detector body including means for generating a light beam to be sensed by said sensor when a tube is in said verification location.

5. The detector as defined in claim 4 including said reader arm second end blocking said light beam when a tube is not in said verification location and said reader arm pivoting when a tube is in said verification location to move said second end out of said light beam to be sensed by said sensor.

6. The detector as defined in claim 1 including said adjustment arm bearing against tubes which are greater than said predetermined size to pivotably adjust for said tube size and to adjust said sensor for said tube size.

7. The detector as defined in claim 6 including said adjustment arm remaining in said adjusted position while said tube is verified in said verification location by said sensor.

* * * * *